(12) United States Patent
Waga et al.

(10) Patent No.: US 9,689,025 B2
(45) Date of Patent: Jun. 27, 2017

(54) NUCLEIC ACID ELEMENT FOR USE IN ANALYSIS, AND ANALYTICAL METHOD, ANALYTICAL REAGENT, AND ANALYTICAL INSTRUMENT USING SAME

(75) Inventors: Iwao Waga, Koto-ku (JP); Jou Akitomi, Koto-ku (JP); Makio Furuichi, Koto-ku (JP)

(73) Assignee: NEC Solution Innovators, Ltd., Tokyo (JP)

( * ) Notice: Subject to any disclaimer, the term of this patent is extended or adjusted under 35 U.S.C. 154(b) by 0 days.

(21) Appl. No.: 13/389,222

(22) PCT Filed: Aug. 6, 2010

(86) PCT No.: PCT/JP2010/063424
§ 371 (c)(1),
(2), (4) Date: Apr. 20, 2012

(87) PCT Pub. No.: WO2011/016565
PCT Pub. Date: Feb. 10, 2011

(65) Prior Publication Data
US 2012/0202195 A1    Aug. 9, 2012

(30) Foreign Application Priority Data
Aug. 7, 2009  (JP) .................................. 2009-185283

(51) Int. Cl.
*C12N 15/11*   (2006.01)
*C12Q 1/68*    (2006.01)
*C12N 15/115*  (2010.01)

(52) U.S. Cl.
CPC .......... *C12Q 1/6825* (2013.01); *C12N 15/115* (2013.01); *C12N 2310/3519* (2013.01); *C12N 2320/10* (2013.01)

(58) Field of Classification Search
None
See application file for complete search history.

(56) References Cited

U.S. PATENT DOCUMENTS

| | | |
|---|---|---|
| 5,424,186 A | 6/1995 | Fodor et al. |
| 5,807,522 A | 9/1998 | Brown et al. |
| 6,242,246 B1 | 6/2001 | Gold et al. |
| 6,458,543 B1 | 10/2002 | Gold et al. |
| 6,503,715 B1 | 1/2003 | Gold et al. |
| 6,544,776 B1 | 4/2003 | Gold et al. |
| 2002/0034747 A1 | 3/2002 | Bruchez, Jr. et al. |
| 2002/0039732 A1 | 4/2002 | Bruchez et al. |
| 2003/0165951 A1 | 9/2003 | Bruchez, Jr. et al. |
| 2004/0171039 A1 | 9/2004 | Bruchez et al. |
| 2008/0254446 A1* | 10/2008 | Sode et al. ......................... 435/6 |
| 2010/0021899 A1 | 1/2010 | Ikebukuro et al. |
| 2010/0304499 A1 | 12/2010 | Oyama et al. |
| 2011/0045484 A1 | 2/2011 | Sode et al. |

FOREIGN PATENT DOCUMENTS

| | | |
|---|---|---|
| JP | 10503841 A | 4/1998 |
| JP | 2004500109 A | 1/2004 |
| JP | 2009133712 A | 6/2009 |
| JP | 2009159965 A | 7/2009 |
| WO | 01/57259 A1 | 8/2001 |
| WO | 0171044 A1 | 9/2001 |
| WO | 2004081235 A1 | 9/2004 |
| WO | 2005049826 A1 | 6/2005 |
| WO | 2006/048164 A1 | 5/2006 |
| WO | 2006078660 A2 | 7/2006 |
| WO | 2008038696 A1 | 4/2008 |
| WO | 2008/111818 A1 | 9/2008 |

OTHER PUBLICATIONS

Wetmur, Critical Reviews in Biochemistry and Molecular Biology, 1991, vol. 26, pp. 227-259.*
Li et al., Chem. Asain J., 2009, vol. 4, pp. 918-922.*
Willner et al., Chemical Society Reviews, 2008, vol. 37, pp. 1153-1165.*
Teller et al., Anal. Chem., 2009, vol. 81, pp. 9114-9119.*
Ali, et al. "Colorimetric Sensing by Using Allosteric-DNAzyme-Coupled Rolling Circle Amplification and a Peptide Nucleic Acid-Organic Dye Probe", Angew. Chem. Int. Ed., 2009, vol. 48, pp. 3512-3515.
Tao, et al. "Label-Free Colorimetric Detection of Aqueous Mercury Ion ($Hg^{2+}$) using $Hg^{2+}$—Modulated G-Quadruplex-Based DNAzymes", Analytical Chemistry, 2009, vol. 81, No. 6, pp. 2144-2149.
Ihara: "Functional Nucleic Acids as Analytical Tools", Bunseki, 2009, The Japan Society for Analytical Chemistry, vol. 9, pp. 520-521.
Ito, Yoshihiro. "Design and synthesis of functional polymers by in vitoro selection", Polymers for Advanced Technologies, 2004, vol. 15, No. ½, pp. 3-14.
Teller, et al. "Aptamer-DNAzyme Hairpins for Amplified Biosensing", Analytical Chemistry, 2009, vol. 81, No. 21, pp. 9114-9119.
Cheng, et al. "General Peroxidase Activity of G-Quadruplex-Hemin Complexes and Its Application in Ligand Screening", Biochemistry, 2009, vol. 48, No. 33, pp. 7817-7823.
Travascio, et al. "DNA-enhanced peroxidase activity of a DNA aptamer-hemin complex", Chemistry & Biology, 1998, vol. 5, No. 9, pp. 505-517.
Yoshida et al.; "Aptameric Enzyme Subunit for Biosensing Based on Enzymatic Activity Measurement"; Analytical Chemistry; May 15, 2006; vol. 78, No. 10, pp. 3296-3303.

(Continued)

*Primary Examiner* — Mindy G Brown
(74) *Attorney, Agent, or Firm* — Sughrue Mion, PLLC

(57) ABSTRACT

The technique by which simple analysis of an intended subject to be analyzed can be carried out is provided. In this technique, a nucleic acid element 16 for use in analysis including: a first nucleic acid part 12; and a second nucleic acid part 13 is used. In the nucleic acid element 16, the first nucleic acid part 12 is a binding part that can bind to a subject 11 to be analyzed, and the second nucleic acid part 13 is a labeling part that can distinguish between binding and non-binding of the first nucleic acid part 12 to the subject 11. It is preferred that the first nucleic acid part 12 is an aptamer against the subject 11. The subject 11 can be analyzed easily by using the nucleic acid element 16, binding the subject 11 to the first nucleic acid part 12, and then analyzing the binding with the second nucleic acid part 13.

9 Claims, 6 Drawing Sheets

(56) References Cited

OTHER PUBLICATIONS

Chen et al.; "A new method for the detection of ATP using a quantum-dot-tagged aptamer"; Analytical and Bioanalytical Chemistry; Oct. 15, 2008; vol. 392, No. 6, pp. 1185-1188.
Bockisch et al.; "Immobilized stem-loop structured probes as conformational switches for enzymatic detection of microbial 16S rRNA"; Nucleic Acids Research; Oxford University Press; Jun. 24, 2005; vol. 33, No. 11, pp. E101.1-E101.8.
Ogasawara et al.; "Detection system based on the conformational change in an aptamer and its application to simple bound/free separation"; Biosensors and Bioelectronics; Elsevier B.V.; Aug. 20, 2008; vol. 24, No. 5, pp. 1372-1376.
Yang et al.; "Real-time PCR detection of protein analytes with conformation-switching aptamers"; Analytical Biochemistry; Elsevier Inc.; May 20, 2008; vol. 380, No. 2, pp. 164-173.
Nutiu et al.; "Structure-Switching Signaling Aptamers: Transducing Molecular Recognition into Fluorescence Signaling"; Chemistry—A European Journal; 2004; vol. 10, No. 8, pp. 1868-1876.
Extended European Search Report for corresponding European Application No. 10806564.0 issued on Aug. 22, 2013.
Li Shen et al., "Electrochemical DNAzyme Sensor for Lead Based on Amplification of DNA—Au Bio-Bar Codes", Anal. Chem., 2008, vol. 80, No. 16, pp. 6323 to 6328.
Lin et al., "Structural basis of DNA folding and recognition in an AMP-DNA aptamer complex: distinct architectures but common recognition motifs for DNA and RNA aptamers complexed to AMP", Chemistry & Biology, 1997, vol. 4, No. 11, pp. 817-832.
Communication dated Sep. 16, 2015, issued by the Japan Patent Office in corresponding Japanese Application No. 2011-525959.
Liu et al., "Functional Nucleic Acid Sensors", Chemical Review, May 2009, vol. 109, No. 5, pp. 1948-1998 (116 pages total).
Xiao et al., "Catalytic Beacons for the Detection of DNA and Telomerase Activity", Journal of American Chemical Society, May 28, 2004, vol. 126, No. 24, pp. 7430-7431.

\* cited by examiner

NUCLEIC ACID ELEMENT FOR USE IN ANALYSIS, AND ANALYTICAL METHOD, ANALYTICAL REAGENT, AND ANALYTICAL INSTRUMENT USING SAME

CROSS REFERENCE TO RELATED APPLICATIONS

This application is a National Stage of International Application No. PCT/JP2010/063424 filed Aug. 6, 2010, claiming priority based on Japanese Patent Application No. 2009-185283 filed Aug. 7, 2009, the contents of all of which are incorporated herein by reference in their entirety.

TECHNICAL FIELD

The present invention relates to a nucleic acid element for use in analysis, and an analytical method, an analytical reagent, and an analytical instrument using the same.

BACKGROUND ART

Recently, cases involving food such as misrepresentation cases and pesticide contamination cases have occurred. Further, cases of food poisoning caused by microorganisms such as *Escherichia coli* O157 strains and *Salmonella enterica*, and food-borne infectious diseases such as Creutzfeldt-Jakob disease caused by pathogenic protein and the like have occurred. Furthermore, accompanying the arrival of an aging society, public health consciousness is spreading. Because of this, public awareness on food is high, and safe and healthy food is required. In order to ensure the quality of food, a system for inspecting the quality of food is necessary in a food production step, a food distribution step, and a food consumption step. On the other hand, as a method for specifically detecting a specific substance, there is a method utilizing an antigen-antibody reaction. For example, the patent document 1 discloses a method for inspecting components in food, using an antigen-antibody reaction.

PRIOR ART DOCUMENTS

Patent Document

Patent Document 1: JP 2009-133712 A

SUMMARY OF INVENTION

Problem to be Solved by the Invention

Sanitation inspections and contamination inspections are carried out in the food production step because of the requirement by the food sanitation law and the voluntary management by food companies and the like. However, it is rare that the quality of food is inspected in the food distribution step and the food consumption step. That is, introducing the same food inspection system as used in food factories into supermarkets, department stores, convenience stores, restaurants, and the like is unrealistic. Furthermore, it is the fact that inspections of chemical substances such as pesticides are rarely carried out even in the food production step. This is because the methods of the inspections are complicated. Moreover, in the method utilizing the antigen-antibody reaction, a subject to be inspected is limited. For example, low-molecular weight compounds such as pesticides are difficult to be recognized as antigens in animals, and toxic substances are fatal to animals for obtaining antibodies. Moreover, it is difficult to make the means utilizing an antigen-antibody reaction into a simple inspection system. Such a simple inspection system is required in not only a food field, but also all fields relating to public health, such as a medical field and an agricultural field.

Hence, the present invention is intended to provide a technique by which simple analysis of an intended subject to be analyzed can be carried out.

Means for Solving Problem

The present invention provides a nucleic acid element for use in analysis, the nucleic acid element including: a first nucleic acid part; and a second nucleic acid part, wherein the first nucleic acid part is a binding part that can bind to a subject to be analyzed, and the second nucleic acid part is a labeling part that can distinguish between binding and non-binding of the first nucleic acid part to the subject.

The present invention further provides an analytical method using the nucleic acid element according to the present invention, the analytical method comprising: binding a subject to be analyzed to a first nucleic acid part; and analyzing the binding with a second nucleic acid part.

The present invention further provides an analytical reagent containing the nucleic acid element according to the present invention.

The present invention further provides an analytical instrument including the analytical reagent according to the present invention.

Effects of the Invention

According to the present invention, simple analysis of a subject to be analyzed can be carried out. Moreover, aptamers are obtained in a test tube, so that, for example, unlike antibodies, aptamers against compounds having high toxicity and aptamers that specifically recognize low-molecular compounds can be obtained. Therefore, for example, by applying a technology of aptamers to the present invention, problems in the means using an antigen-antibody reaction can be solved, and a simple detection system can be developed in a field such as a food field and the like.

DESCRIPTION OF EMBODIMENTS

Figure 1A:
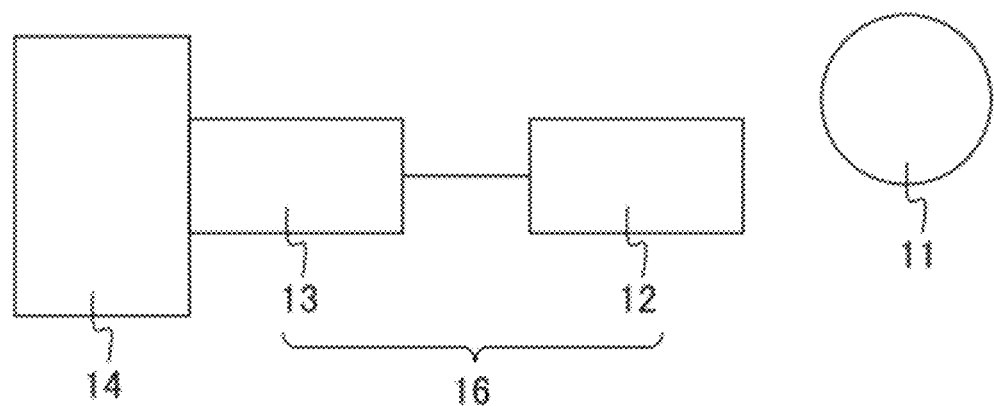
FIGS. 1A and 1B are explanatory drawings schematically illustrating a nucleic acid element for use in analysis of the first embodiment of the present invention.

<Nucleic Acid Element for Use in Analysis>

The nucleic acid element for use in analysis of the present invention is characterized in that it includes: a first nucleic acid part; and a second nucleic acid part, the first nucleic acid part is a binding part that can bind to a subject to be analyzed, and the second nucleic acid part is a labeling part that can distinguish between binding and non-binding of the first nucleic acid part to the subject. In the present invention, "analysis" encompasses quantitative analysis, semi-quantitative analysis, and qualitative analysis (the same applies hereinafter).

Each of the first nucleic acid part and the second nucleic acid part includes a nucleic acid molecule and may be composed of only the nucleic acid molecule or may contain the same, for example. In the nucleic acid element of the present invention, it is preferred that the first nucleic acid part includes a nucleic acid molecule whose structure is changed by binding to the subject, and the second nucleic acid part includes a nucleic acid molecule whose structure is changed by the change in the structure of the first nucleic acid part.

The first nucleic acid part is, as mentioned above, the binding part of binding the subject in the nucleic acid element. The first nucleic acid part includes, as the nucleic acid molecule, a nucleic acid molecule that can bind to the subject, for example. Hereinafter, the nucleic acid molecule that can bind to the subject is also referred to as the "subject-bindable nucleic acid molecule", for example. The first nucleic acid part may be composed of only the subject-bindable nucleic acid molecule or may contain the same, for example.

The second nucleic acid part is, as mentioned above, a labeling part that can distinguish between binding and non-binding in the nucleic acid element. Examples of the second nucleic acid part include the following two forms.

A first form of the second nucleic acid part is a form with which the second nucleic acid part can bind to a labeling substance, for example. Binding and non-binding of the first nucleic acid part to the subject can be distinguished by determining whether or not the labeling substance binds to the second nucleic acid part, for example. The second nucleic acid part includes, as the nucleic acid molecule, a nucleic acid molecule that can bind to the labeling substance, for example. Hereinafter, the nucleic acid molecule that can bind to the labeling substance is also referred to as the "labeling substance-bindable nucleic acid molecule". The second nucleic acid part may be composed of or may contain the labeling substance-bindable nucleic acid molecule, for example. The labeling substance is not particularly limited and can be, for example, an enzyme as mentioned below.

A second form of the second nucleic acid part is a form with which the second nucleic acid part itself can distinguish between binding and non-binding of the first nucleic acid part to the subject, for example. The second nucleic acid part includes, as the nucleic acid molecule, a nucleic acid molecule that can generate a catalytic function of enzyme, for example. The nucleic acid molecule that can generate the catalytic function of enzyme is also referred to as the "catalyst nucleic acid molecule". The second nucleic acid part may be composed of only the catalyst nucleic acid molecule or may contain the same, for example.

The subject-bindable nucleic acid molecule, the labeling substance-bindable nucleic acid molecule, and the catalyst nucleic acid molecule are described below. They are, however, by no means limited thereto.

A component of each of the nucleic acid molecules is not particularly limited. The component can be, for example, a nucleotide residue. Examples of the nucleotide residue include a ribonucleotide residue and a deoxyribonucleotide residue. Each of the nucleic acid molecules may be, for example, RNA composed of a ribonucleotide residue, DNA composed of a deoxyribonucleotide residue, or a nucleic acid molecule containing both of deoxyribonucleotide and ribonucleotide. Examples of the component also include monomer residues such as PNA (peptide nucleic acid), LNA (locked nucleic acid), and ENA (2'-O,4'-C-ethylenebridged nucleic acids). Each of the nucleic acid molecules contains, for example, these monomer residues.

The nucleotide residue may be, for example, a modified nucleotide residue. The modified nucleotide residue can be, for example, the one obtained by modifying a sugar residue of the nucleotide residue. Examples of the sugar residue include a ribose residue and a deoxyribose residue. A modification site in the nucleotide residue is not particularly limited and can be, for example, the 2' position and/or the 4' position of the sugar residue. Examples of the modification include methylation, fluorination, amination, and thiation. Specific examples of the modified nucleotide residue include those each obtained by modifying the 2'-position of the ribose residue, such as 2'-fluorouracil (2'-fluorinatd-uracil nucleotide residue), 2'-aminouracil (2'-aminated-uracil-nucleotide residue), 2'-O-methyluracil (2'-methylated-uracil nucleotide residue), and 2'-thiouracil (2'-thiated-uracil nucleotide residue).

Each of the nucleotide acid molecules may be, for example, a single-stranded nucleic acid or a double-stranded nucleic acid. Examples of the single-stranded nucleic acid include a single-stranded RNA and a single-stranded DNA. Examples of the double-stranded nucleic acid include a double-stranded RNA, a double-stranded DNA, and a double-stranded nucleic acid of RNA and DNA. Each of the nucleotide acid molecules is preferably a single-stranded nucleic acid, for example.

In each of the nucleic acid molecules, bases may be, for example, natural bases (non-artificial bases) such as adenine (a), cytosine (c), guanine (g), thymine (t), and uracil (u) or non-natural bases (artificial bases). Examples of the artificial bases include modified bases and altered bases, and it is preferred that they have the same functions as the natural bases (a, c, g, t, and u). Examples of the artificial bases having the same functions as the natural bases include an artificial base capable of binding to cytosine (c) substituted for guanine (g), an artificial base capable of binding to guanine (g) substituted for cytosine (c), an artificial base capable of binding to thymine (t) or uracil (u) substituted for adenine (a), an artificial base capable of binding to adenine (a) substituted for thymine (t), and an artificial base capable of binding to adenine (a) substituted for uracil (u). Examples of the modified bases include methylated bases, fluorinated bases, aminated bases, and thiated bases. Specific examples of the modified bases include 2'-fluorouracil, 2'-aminouracil, 2'-O-methyluracil, and 2-thiouracil. In the present invention, for example, bases represented by a, g, c, t, and u mean, in addition to the natural bases, the artificial bases having the same functions as the natural bases.

Each of the nucleic acid molecules may have a secondary structure formed by self-annealing, for example. The secondary structure can be, for example, a stem-loop structure.

Each of the nucleic acid molecules may have, for example, a naturally-derived nucleic acid sequence or a synthesized nucleic acid sequence. A method for synthesizing each of the nucleic acid molecules is not at all limited and can be, for example, a method in which a nucleic acid molecule is chemically synthesized from terminal bases using dNTP, NTP, or the like as a material by a DNA synthesizer or an RNA synthesizer.

The subject-bindable nucleic acid molecule and the labeling substance-bindable nucleic acid molecule are preferably aptamers, for example. The aptamers generally mean nucleic acid molecules that can bind to a specific target.

A method for producing aptamers is not particularly limited, and they can be produced by the above-mentioned conventionally known method, for example. In the production of aptamers, the conventionally known SELEX (systematic evolution of ligands by exponential enrichment) method or the like can be employed, for example.

The preparation of aptamers by the SELEX method is not particularly limited and can be carried out as follows, for example. First, a nucleic acid pool and a target are prepared. The nucleic acid pool is, for example, a nucleic acid library containing a plurality of nucleic acid molecules. The target is not particularly limited, and is, for example, the subject when aptamers that can bind to the subject are prepared and the labeling substance when aptamers that can bind to the labeling substance are prepared. Then, the nucleic acid pool and the target are bound to (associated with) each other so as to form a composite of them. Thereafter, nucleic acid molecules that can bind to the target can be selected as the aptamers that can bind to the target by collecting only a nucleic acid pool involved in the formation of the composite.

A method for preparing aptamers that can bind to a target, using the SELEX method is shown below as an example. The present invention, however, is by no means limited thereto.

The nucleic acid pool is, for example, a library (mixture) of a plurality of nucleic acid molecules each having a random region. Examples of the nucleic acid molecules in the library include polynucleotides such as RNAs and DNAs. The random region is, for example, a region in which bases of A, G, C, and U or bases of A, G, C, and T are randomly linked, and the length thereof is, for example, in the range from 20 to 120 mer. The nucleic acid pool includes preferably from $4^{20}$ to $4^{120}$ types (about from $10^{12}$ to $10^{72}$ types) of nucleic acid molecules, more preferably from $4^{30}$ to $4^{60}$ types (about from $10^{18}$ to $10^{36}$ types) of nucleic acid molecules.

It is only necessary that each of the polynucleotides contained in the nucleic acid pool has the random region, for example, and the other configuration is not particularly limited. It is preferred that each of the polynucleotides has, for example, in addition to the random region, a primer region to which a primer can anneal, a polymerase recognition region that can be recognized by a polymerase, and the like, at least one of the 5'-end and 3'-end of the random region. The polymerase recognition region can be decided as appropriate according to the type of polymerase used in a nucleic acid amplification described below, for example. In the case where the nucleic acid pool is an RNA pool, the polymerase recognition region is, for example, preferably a DNA-dependent RNA polymerase recognition region (hereinafter, also referred to as an "RNA polymerase recognition region"), and specifically, a T7 promoter that is a T7 RNA polymerase recognition region. A specific example of the RNA pool can be, for example, an RNA pool containing RNAs each having a structure in which, from the 5'-end side thereof, the RNA polymerase recognition region and the primer region (hereinafter, also referred to as a "5'-end side primer region") are linked in this order, the random region is linked to the 3' end side of the 5'-end side primer region, and the primer region (hereinafter, also referred to as a "3'-end side primer region") is linked to the 3' end side of the random region. It is preferred that the 5'-end side primer region in the RNA is, for example, a sequence complementary to the 3' side of a DNA antisense strand synthesized using the RNA as a template, i.e., a sequence that is the same as a sequence of a primer that can bind to the 3' side of the antisense strand. Moreover, the RNA pool may further include a region that assists the binding to a target, for example. Each of the polynucleotides in the nucleic acid pool may have a different random sequence or a random sequence a part of which is a common sequence. The respective sequences in each of the polynucleotides may be directly adjoined (linked) to one another or may be indirectly adjoined (linked) through intervening sequences.

A method for preparing the nucleic acid pool is not particularly limited, and a known method can be employed. In the case where the nucleic acid pool is an RNA pool, the nucleic acid pool can be prepared using an initial pool containing DNAs and, as templates, the DNAs, for example. Hereinafter, a DNA strand used as a template of RNAs in a nucleic acid pool is also referred to as an antisense strand, and a DNA strand having a sequence of any of the RNAs with U replaced by T is also referred to as a sense strand. It is preferred that the initial pool containing DNAs contains, for example, any of DNAs (antisense strands) each obtained by replacing U in a strand complementary to each random region in the RNA pool by T and DNAs (sense strands) each having a sequence obtained by replacing U in each random region by T. A nucleic acid amplification is conducted using each of the DNAs in this initial pool as a template and a DNA-dependent DNA polymerase. Thereafter, a transcription reaction is conducted using each of obtained DNA amplification products as a template and a DNA-dependent RNA polymerase. Thus, a nucleic acid pool containing RNAs is prepared.

It is also possible that a nucleic acid pool containing RNAs is prepared by a nucleic acid amplification through a preparation of an initial pool containing DNAs each obtained by replacing U in each random region of each of the RNAs by T and annealing of primers each having an RNA polymerase recognition region and a sequence complementary to a 5'-end side primer region, using the initial pool as a template.

Then, the nucleic acid pool and a target react with each other. Thus, a composite of the nucleic acid pool and the target is formed. In the preparation of aptamers, the target that reacts with the nucleic acid pool may be, for example, the above-described target or a degradate thereof. A binding form between the nucleic acid pool and the target is not particularly limited and can be, for example, a bond via intermolecular force such as a hydrogen bond. A treatment for binding between the nucleic acid pool and the target can be, for example, a method in which the nucleic acid pool and the target are incubated for a certain period of time in a solvent. The solvent is not particularly limited and preferably the one can maintain the bond between the nucleic acid pool and the target and the like. Examples of the solvent include various buffer solutions.

Subsequently, the composite of the nucleic acid pool and the target is collected. A reaction solution in which the nucleic acid pool and the target is caused to react with each other in order to form a composite of them contains, besides the composite, a nucleic acid pool (hereinafter referred to as a "unreacted nucleic acid pool") that does not involved in formation of the composite, for example. Therefore, for example, it is preferred that the composite and the unreacted nucleic acid pool in the reaction solution are separated from each other. A method for separating the composite and the unreacted nucleic acid pool from each other is not particularly limited and can be, for example, a method utilizing the difference in adsorbability between the target and the nucleic acid pool or the difference in molecular weight between the composite and the nucleic acid pool.

As the former method utilizing the difference in adsorbability, the following method is illustrative, for example. First, a carrier having adsorbability to the target and the reaction solution containing the composite are brought into contact with each other. In this case, the unreacted nucleic acid pool is not adsorbed to the carrier. In contrast, the composite of the target and the nucleic acid pool is adsorbed to the same. Thus, the unreacted nucleic acid pool and the composite can be separated from each other. Therefore the composite adsorbed to the carrier can be collected after removing the unreacted nucleic acid pool. It is preferred that the carrier is washed in order to completely remove the unreacted nucleic acid pool prior to collection of the composite from the carrier, for example. The carrier having adsorbability to the target is not particularly limited and can be selected as appropriate according to the type of the target, for example. In the case where the target is, for example, a protein such as an antibody, the carrier having the adsorbability can be, for example, a nitrocellulose film.

As the latter method utilizing the difference in molecular weight, a method using a carrier can be illustrative, for example. The carrier can be, for example, a carrier having pores each with a pore size with which the nucleic acid pool is allowed to pass therethrough, but the composite is not allowed to pass therethrough. By utilizing such a carrier, the composite and the unreacted nucleic acid pool can be separated from each other. The separation may be, for example, electrical separation using an agarose gel, a polyacrylamide gel, or the like.

Besides these methods, the method for separating the composite and the unreacted nucleic acid from each other can be, for example, a method using a target immobilized on a carrier in formation of composite. The target is previously immobilized on a carrier, and the carrier and the nucleic acid pool are brought into contact with each other. Thus, a composite of the immobilized target and the nucleic acid pool is formed. Then, an unreacted nucleic acid pool binding to no immobilized target is removed, and thereafter the composite of the target and the nucleic acid pool is dissociated from the carrier and collected. A method for immobilizing the target on the carrier is not at all limited, and a known method can be employed. Specifically, the method can be, for example, a method in which the target is previously bound to a label, and a carrier having a ligand with the label and the target binding to the label are brought into contact with each other. The label can be, for example, a His-tag. Examples of the ligand include metal ions such as a nickel ion ($Ni^{2+}$) and a cobalt ion ($Co^{2+}$). Specific examples of the carrier include Ni-agarose and Ni-sepharose based on the metal ions.

Then, a nucleic acid pool involved in formation of the composite is collected from the collected composite. The nucleic acid pool involved in formation of the composite can be collected by releasing a bond between the target and the nucleic acid pool, for example.

Subsequently, a nucleic acid amplification of the collected nucleic acid pool involved in formation of the composite is conducted. A method for amplifying the nucleic acid pool is not particularly limited, and the nucleic acid pool can be amplified by a known method according to the type of the nucleic acid pool, for example. In the case where the nucleic acid pool is an RNA pool, for example, first, cDNAs are prepared by a reverse transcription reaction using an RNA-dependent DNA polymerase, and a nucleic acid amplification of DNAs is conducted by a PCR or the like using the each of the cDNAs as a template. Then, using each of amplification products thus obtained as a template and using, for example, a DNA-dependent RNA polymerase, a transcription of RNAs is conducted. Thus, the RNA pool involved in formation of the composite can be amplified.

When each of the RNAs in the RNA pool contains an RNA polymerase recognition region, a 5'-end side primer region, a random region, and a 3'-end side primer region, the nucleic acid amplification can be conducted by an amplification method utilizing these regions, for example. In a reverse transcription reaction for preparing the cDNAs using each of the RNAs as a template, it is preferred that a polynucleotide having a sequence complementary to the 3'-end side primer region contained in the RNA pool is used as a primer, for example. Further, in an amplification of DNAs using each of the cDNAs as a template, it is preferred that a polynucleotide having the 5'-end side primer region and a polynucleotide having a strand complementary to the 3'-end side primer region are used as primers, for example. It is preferred that the former polynucleotide further has the RNA polymerase recognition region on the 5'-end side thereof and the 5'-end side primer region on the 3' end side thereof, for example. In an amplification of RNAs using each of obtained amplification products of DNAs as a template, a nucleic acid amplification such as a PCR is conducted using each of the DNA amplification products as a template, a 5'-end side primer region and the 3'-end side primer region in each of the DNAs, and a DNA-dependent DNA polymerase. In this case, for example, it is preferred that, in the amplification, a polynucleotide containing the 5'-end side primer region and a polynucleotide containing a strand complementary to the 3'-end side primer region are used as primers. Further, it is preferred that the former polynucleotide has the RNA polymerase recognition region on the 5'-end side thereof and the 5'-end side primer region on the 3' end side thereof, for example. Then, a transcription reaction in vitro is conducted using each of obtained amplification products as a template, the RNA polymerase recognition region in each of the amplification products, and the DNA-dependent RNA polymerase. Thus, a nucleic acid amplification of the RNA pool involved in formation of the composite can be conducted. In each of the amplification products, a DNA of an antisense strand has an RNA polymerase recognition region on the 3' end side thereof, for example. Therefore, the DNA-dependent RNA polymerase is bound to this region, and each of the RNAs can be synthesized using the antisense strand as a template. The RNA-dependent DNA polymerase used in the reverse transcription reaction is not particularly limited, and a reverse transcriptase derived from avian myeloblastosis virus (AMV Reverse Transcriptase) can be used, for example.

The method for amplifying nucleic acids is not particularly limited, and for example, any of a PCR method and various isothermal amplification methods can be employed. The conditions thereof are also not particularly limited.

As described above, a nucleic acid pool forming a composite with a target is collected. Further, as mentioned above, formation of composite using a target, collection of the composite, separation of a nucleic acid pool involved in formation of the composite, an amplification of the separated nucleic acid pool, and the like are repeated. Thus, nucleic acid aptamers having binding properties to the target can be eventually obtained.

The catalyst nucleic acid molecule can be, as mentioned above, a nucleic acid molecule that can generate a catalytic function of enzyme. The catalytic function is not particularly limited and is, for example, a catalytic function in an oxidation-reduction reaction. In the nucleic acid element, for example, the catalytic function of the catalyst nucleic acid molecule is inhibited or inactivated when the subject binds to the first nucleic acid part, and the inhibition of the catalytic function is removed, or the catalytic function is activated when the subject binds to the first nucleic acid part.

The oxidation-reduction reaction can be, for example, a reaction in which, in a step of generating products from substrates, transfer of electrons between two substrates is generated. The type of the oxidation-reduction reaction is not particularly limited. The nucleic acid molecule that can generate a catalytic function of the oxidation-reduction reaction can be, for example, the one exerts the same activity as an enzyme that catalyzes the oxidation-reduction reaction. Specifically, the nucleic acid molecule can be, for example, a nucleic acid molecule having peroxidase activity, phosphatase activity, or ribonuclease activity. The peroxidase activity can be, for example, horseradish-derived peroxidase (HRP) activity. Among nucleic acid molecules having the same catalytic function as the enzyme, DNA is referred to as DNA enzyme or DNAzyme, and RNA is referred to as RNA enzyme or RNAzyme, for example.

The catalyst nucleic acid molecule is a nucleic acid molecule that forms a structure of preferably G-quartet (or G-tetrad), more preferably a guanine quadruplex (or G-quadruplex). The G-tetrad is, for example, a structure of a plane of guanine when the guanine is tetramer, and the G-quadruplex is, for example, a structure in which a plurality of the G-tetrads are overlapped. The G-tetrad and the G-quadruplex are formed in a nucleic acid molecule having a structural motif of G-rich when replicated, for example. Examples of the G-tetrad include a parallel-type G-tetrad and anti-parallel-type G-tetrad, and it is preferably the parallel-type G-tetrad. In the nucleic acid element, it is preferred that formation of the G-tetrad is inhibited when the subject does not bind to the first nucleic acid part, and the inhibition is removed, and the G-tetrad is formed when the subject binds to the first nucleic acid part, for example.

The catalyst nucleic acid molecule is preferably a nucleic acid molecule that can bind to porphyrin, specifically a nucleic acid molecule that forms the G-tetrad and can bind to the porphyrin. It is known that the nucleic acid molecule having the G-tetrad generates a catalytic function such as an oxidation-reduction reaction by forming a composite with the porphyrin through binding to the porphyrin, for example. In the nucleic acid element, it is preferred that binding of the catalyst nucleic acid molecule to porphyrin is inhibited when the subject does not bind to the first nucleic acid part, and the inhibition is removed, and the catalyst nucleic acid molecule binds to the porphyrin when the subject binds to the first nucleic acid part, for example. Specifically, in the nucleic acid element, it is preferred that, when the subject does not bind to the first nucleic acid part, formation of the G-tetrad in the catalyst nucleic acid molecule is inhibited, and thus binding of the catalyst nucleic acid molecule to the porphyrin is inhibited, and when the subject binds to the first nucleic acid part, the G-tetrad is formed, and the catalyst nucleic acid molecule binds to the porphyrin, for example.

The porphyrin is not particularly limited, and examples thereof include unsubstituted porphyrin and a derivative thereof. Examples of the derivative include substituted porphyrin and metal porphyrin obtained by forming a composite with a metal element. The substituted porphyrin can be, for example, N-methylmesoporphyrin. The metal porphyrin can be, for example, hemin that is a ferric composite. The porphyrin is, for example, preferably the metal porphyrin, more preferably hemin.

The catalyst nucleic acid molecule is not at all limited as mentioned above. As DNA having peroxidase activity, DNAzyme disclosed in the following literatures (1) to (4) are illustrative, for example. DNAzyme disclosed in these literatures can generate higher peroxidase activity by forming a composite with porphyrin such as hemin as compared with hemin alone,
(1) Travascio et al., Chem. Biol., 1998, vol. 5, pp. 505-517
(2) Cheng et al., Biochemistry, 2009, vol. 48, pp. 7817-7823
(3) Teller et al., Anal. Chem., 2009, vol. 81, pp. 9144-9119
(4) Tao et al., Anal. Chem., 2009, vol. 81, pp. 2144-2149.

A method for producing the catalyst nucleic acid molecule is not particularly limited, and the sequence thereof can be designed and synthesized according to the type of the desired oxidation-reduction reaction, for example. In this case, for example, it may be possible that, by a computer or the like, the secondary structure of the catalyst nucleic acid molecule is predicted, and then the sequence is revised.

The nucleic acid element of the present invention may be, for example, an element composed of only the first nucleic acid part and the second nucleic acid part or an element containing, besides them, other component. Examples of the other component include the labeling substance and the porphyrin. The labeling substance is, for example, an optional component and is detachable according to the presence or absence of binding of the subject to the first nucleic acid part. The porphyrin may be present together with the nucleic acid element in analysis, for example.

The other component can be, for example, a linker. The linker can be, for example, a nucleic acid containing a nucleotide. The linker may be a nucleic acid composed of only a nucleotide or a nucleic acid containing a nucleotide, for example. The linker may be, for example, a single-stranded nucleic acid or a double-stranded nucleic acid. In the case where the linker is a single-stranded nucleic acid, examples thereof include a single-stranded DNA and a single-stranded RNA. In the case where the linker is a double-stranded nucleic acid, examples thereof include a double-stranded DNA, a double-stranded RNA, and a DNA-RNA double strand. The linker may contain, as bases, the above-mentioned natural bases or non-natural bases. The linker may contain, for example, PNA or LNA. The length of the linker is not particularly limited.

In the nucleic acid element of the present invention, it is preferred that the first nucleic acid part and the second nucleic acid part are linked to each other. For example, one end of the first nucleic acid part and one end of the second nucleic acid part are linked to each other. With respect to the linkage between the first nucleic acid part and the second nucleic acid part, for example, the 5' end of the first nucleic acid part and the 3' end of the second nucleic acid part may be linked to each other, or the 3' end of the first nucleic acid part and the 5' end of the second nucleic acid part may be linked to each other.

The linkage between the first nucleic acid part and the second nucleic acid part may be, for example, a direct linkage or an indirect linkage.

In the case of the direct linkage, one end of the first nucleic acid part and one end of the second nucleic acid part are linked to each other by a phosphodiester bond, for example. Specifically, the direct linkage can be, for example, a linkage between the 5' end of the first nucleic acid part and the 3' end of the second nucleic acid part by a phosphodiester bond or a linkage between the 3' end of the first nucleic acid part and the 5' end of the second nucleic acid part by the same.

In the case of the indirect linkage, the first nucleic acid part and the second nucleic acid part are linked to each other via the linker, for example. Hereinafter, a linker intervening between the first nucleic acid part and the second nucleic acid part is referred to as an intervening linker or an intervening sequence. For example, the intervening linker can take the form in which one end of the intervening linker is linked to one end of the first nucleic acid part, and the other end of the linker is linked to one end of the second nucleic acid part. Specifically, the indirect linkage can be, for example, a linkage in which one end of the intervening linker is linked to the 5' end of the first nucleic acid part and the other end of the linker is linked to the 3' end of the second nucleic acid part or a linkage in which one end of the linker is linked to the 3' end of the first nucleic acid part, and the other end of the linker is linked to the 5' end of the second nucleic acid part. The former is preferable. The linkage between the linker and the first nucleic acid part or the second nucleic acid part can be, for example, a linkage by a phosphodiester bond.

The nucleic acid element may further include a linker on one end side thereof. Hereinafter, this linker is referred to as an additional linker or an additional sequence. The nucleic acid element may include the linker at one end of the first nucleic acid part, opposite to the end to which the second nucleic acid part is linked or at one end of the second nucleic acid part, opposite to the end to which the first nucleic acid part is linked, for example. The nucleic acid element may include the additional linkers both at the one end of the first nucleic acid part and the one end of the second nucleic acid part.

It is preferred that the nucleic acid element of the present invention is a single-stranded nucleic acid including the first nucleic acid part and the second nucleic acid part being linked to each other. When the nucleic acid element of the present invention is a single-stranded nucleic acid as described above, for example, a change in secondary structure of the single-stranded nucleic acid occurs by binding the subject to the first nucleic acid part, and this change is prone to cause a change in secondary structure of the second nucleic acid part.

In the nucleic acid element of the present invention, the lengths of the first nucleic acid part and the second nucleic acid part are not particularly limited. The lower limit of the length of the nucleic acid molecule in the first nucleic acid part is not particularly limited, and is, for example, 7 bases. The upper limit of the same is not particularly limited, and is, for example, 120 bases, preferably 80 bases, more preferably 35 bases, yet more preferably 20 bases, and the shorter the length the better. The range of the length is, for example, from 7 to 120 bases, preferably from 7 to 80 bases, more preferably from 7 to 35 bases, and yet more preferably from 7 to 20 bases. The lower limit of the length of the nucleic acid molecule in the second nucleic acid part is not particularly limited, and is, for example, 7 bases. The upper limit of the same is not particularly limited, and is, for example, 120 bases, preferably 80 bases, more preferably 60 bases, yet more preferably 40 bases, and particularly preferably 35 bases, and the shorter the length the better. The range of the length is, for example, from 7 to 120 bases, preferably from 7 to 80 bases, more preferably from 7 to 60 bases, yet more preferably from 7 to 40 bases, and particularly preferably from 7 to 35 bases. The length of the entire nucleic acid element is not particularly limited, and the range of the length is, for example, from 14 to 240 bases, preferably from 14 to 200 bases, more preferably from 14 to 160 bases, yet more preferably from 14 to 140 bases, particularly preferably from 14 to 75 bases, more particularly preferably from 14 to 55 bases. In the nucleic acid element, the length of the first nucleic acid part may be identical to or different from that of the second nucleic acid part, for example.

In the present invention, the subject is not particularly limited, and examples thereof include high-molecular compounds, low-molecular compounds, organic substances, and inorganic substances. Examples of the high-molecular compounds or the organic substances include microorganisms, virus, polysaccharides, proteins, nucleic acids, and resins. Examples of the low-molecule compounds include pesticides, pharmaceuticals, chemicals, oligosaccharides, monosaccharides, lipids, oligopeptides, amino acids, vitamins, and bioactive substances. Examples of the inorganic substances include minerals, mineral acids, and metals.

In the present invention, a sample to be analyzed is not particularly limited, and examples thereof include food (including beverages), pharmaceuticals, chemicals, the ground, animals, plants, microorganisms, virus, water (e.g., tap water, discharged water, river water, seawater, rainwater, snow, and the like), garbage, and waste.

Specific embodiments of the nucleic acid element of the present invention are shown below. It is to be noted that the present invention is by no means limited thereto.

First Embodiment

A nucleic acid element for use in analysis of the first embodiment includes: a subject-bindable nucleic acid molecule as a first nucleic acid part; and a labeling substance-bindable nucleic acid molecule as a second nucleic acid part. Specifically, the nucleic acid element includes: the first nucleic acid part; and the second nucleic acid part, the second nucleic acid part can bind to a labeling substance when the subject does not bind to the first nucleic acid part, and the second nucleic acid part cannot bind to the labeling substance when the subject binds to the first nucleic acid part.

The "labeling substance" is an optional component of the nucleic acid element of the present invention and is detachable according to the presence or absence of binding of the subject to the first nucleic acid part.

For example, the nucleic acid element can take the form in which a secondary structure of the second nucleic acid part is changed by binding the subject to the first nucleic acid part, and the labeling substance binding to the second nucleic acid part is released from the second nucleic acid part by the change in the secondary structure of the second nucleic acid part. In this case, the labeling substance is, for example, an enzyme. In the nucleic acid element, the enzyme can take the form in which the catalytic function of the enzyme, i.e., the enzyme reaction of the enzyme is inhibited when the enzyme binds to the second nucleic acid part, and the inhibition of the catalytic function, i.e., the inhibition of the enzyme reaction is removed when the enzyme is released from the second nucleic acid part.

The first nucleic acid part may change its structure when the subject binds thereto, for example. Then, the structure of the second nucleic acid part is changed by the change in the structure of the first nucleic acid part, and the labeling part binding to the second nucleic acid part may be released from the second nucleic acid part.

Specific examples of the nucleic acid element of the present embodiment are shown below. The present invention, however, is by no means limited thereto.

Figure 1B:
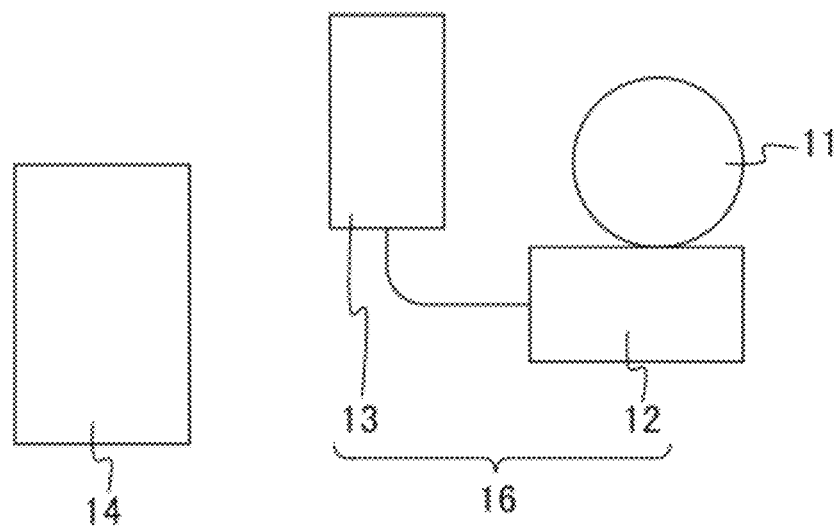

The configuration of the nucleic acid element is schematically shown in FIGS. 1A and 1B. FIG. 1A shows the state where the subject does not bind to the nucleic acid element, and FIG. 1B shows the state where the subject binds to the nucleic acid element.

As shown in FIGS. 1A and 1B, a nucleic acid element 16 for use in analysis is configured so that it includes: a first nucleic acid part (binding part) 12; and a second nucleic acid part (labeling part) 13. The first nucleic acid part 12 is a subject-bindable nucleic acid molecule, and the second nucleic acid part 13 is a labeling substance-bindable nucleic acid molecule. The first nucleic acid part 12 and the second nucleic acid part 13 are integrated by linking to each other. For example, one end of the first nucleic acid part 12 and one end of the second nucleic acid part 13 may be directly linked to each other or indirectly linked to each other via a linker, for example. The linkage between the first nucleic acid part 12 and the second nucleic acid part 13 is not particularly limited. For example, the 5' end of the second nucleic acid part 13 may be linked to the 3' end of the first nucleic acid part 12, or the 3' end of the second nucleic acid part 13 may be linked to the 5' end of the first nucleic acid part 12.

As shown in FIG. 1A, when a subject 11 to be analyzed does not bind to the first nucleic acid 12, a labeling substance 14 binds to the second nucleic acid part 13. As shown in FIG. 1B, when the subject 11 binds to the first nucleic acid part 12, the structure of the second nucleic acid part 13 or the like is changed, whereby the labeling substance 14 is released from the second nucleic acid part 13. In the case where the labeling substance 14 is an enzyme, the catalytic function of the enzyme is inhibited when the enzyme binds to the second nucleic acid part 13, for example. On the other hand, the inhibition of the catalytic function is removed when the enzyme as the labeling substance 14 is released from the second nucleic acid part 13. At that time, when a substrate is present, an enzyme reaction is generated by the catalytic function of the enzyme. Therefore, it becomes possible to analyze the subject 11 through analysis of the enzyme reaction.

A method for analyzing the enzyme reaction is not particularly limited and may be, for example, optical detection or electrochemical detection. The optical detection can be, for example, detection of an optical signal such as a developed color or emitted light and can be carried out by measuring a signal intensity such as an absorbance, a reflectance, or a fluorescence intensity. The optical signal is generated by carrying out the enzyme reaction in the presence of a substrate, for example. The substrate is not particularly limited and is preferably a substrate that develops a color or emits light by the enzyme reaction. The electrochemical detection can be, for example, detection of an electrochemical signal and can be carried out by measuring a signal intensity such as a current. The electrochemical signal is generated, as the transfer of electrons, by carrying out the enzyme reaction in the presence of a substrate, for example. The transfer of electrons can be measured as a current through applying a voltage to electrodes, for example. In the case of the detection of an electrochemical signal, for example, the enzyme reaction may be carried out in the presence of the substrate and a mediator, and at that time, the transfer of electrons between the enzyme and the mediator may be measured.

The substrate is not particularly limited, and is, for example, preferably a chromogenic substrate that develops a color by an enzyme reaction because it allows analysis to be carried out easily. The color development includes coloring, for example. In this case, the enzyme can be, for example, oxidoreductase. In the present invention, the oxidoreductase means an enzyme that catalyzes an oxidation-reduction reaction in a broad sense. Examples of the oxidoreductase include peroxidase and phosphatase. The phosphatase can be, for example, alkaline phosphatase. When the enzyme is peroxidase, examples of the chromogenic substrate includes 3,3',5,5'-tetramethylbenzidine (TMB), 1,2-phenylenediamine (OPD), 2,2'-azinobis (3-ethylbenzothiazoline-6-sulfonic acid ammonium salt (ABTS), 3,3'-diaminobenzidine (DAB), 3,3'-diaminobenzidine tetrahydrochloride hydrate (DAB4HCl), 3-amino-9-ethylcarbazole (AEC), 4-chloro-1-naphthol (4C1N), 2,4,6-tribromo-3-hydroxybenzoic acid, 2,4-dichlorophenol, 4-aminoantipyrine, 4-aminoantipyrine hydrochloride, and luminol. When the enzyme is alkaline phosphatase, examples of the chromogenic substrate include 5-bromo-4-chloro-3-indolylphosphate/nitrotetrazolium blue (Nitro-TB), and nitro-blue tetrazolium chloride (NBT). Each of these chromogenic substrates can be used also in electrochemical detection as a substrate, for example.

The mediator is not particularly limited, and examples thereof include potassium ferricyanide, ferrocene, methyl ferrocene, ferrocene dicarboxylic acid, promazine, tetrathiafulvalene (TTF), methylene blue, 1,4-benzoquinone, 1,4-bis (N,N-dimethylamino)benzene, 4,4-dihydropiphenyl, α-naphthoquinone, and derivatives thereof.

Figure 2A:
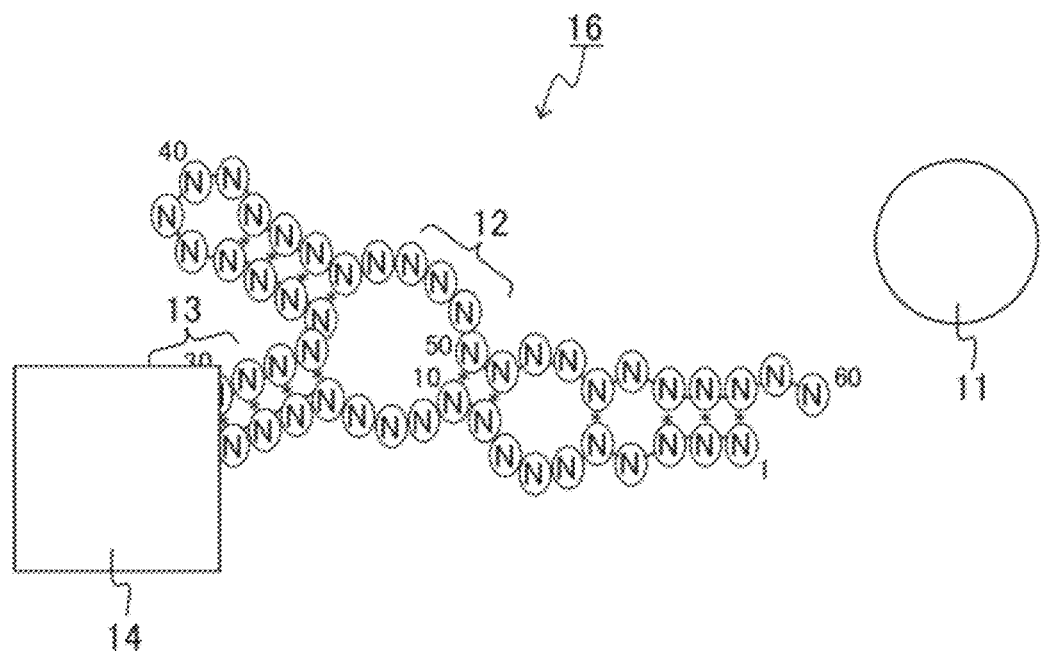
FIGS. 2A and 2B show a specific example of an analytical method using the nucleic acid element of the first embodiment.
Figure 2B:
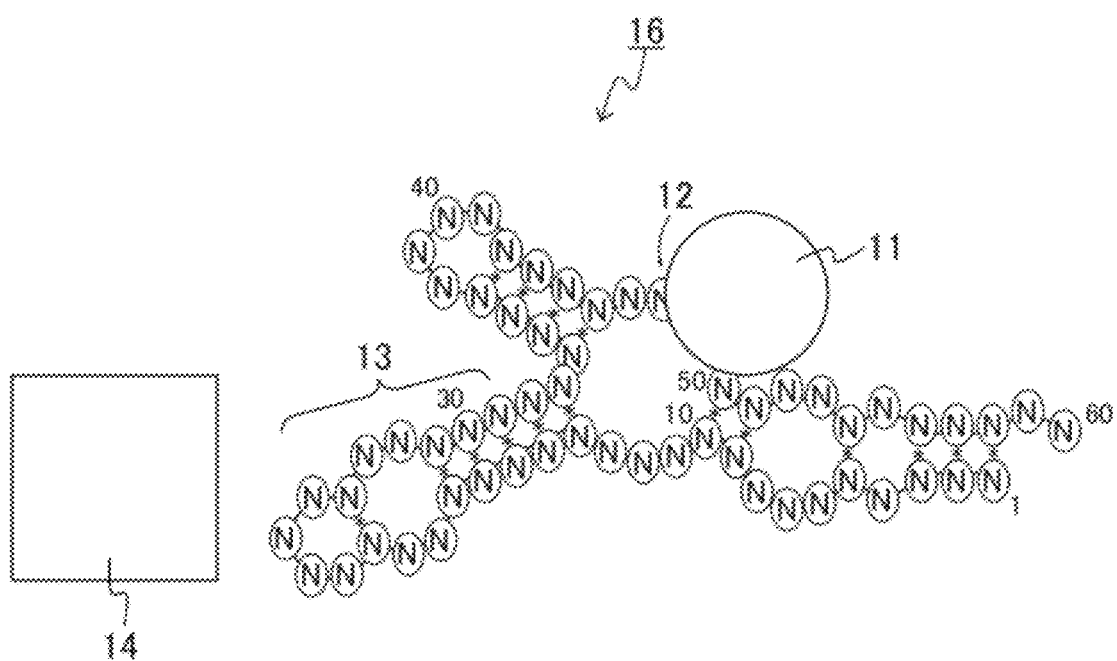

Next, examples of a nucleic acid element 16 for use in analysis, in which aptamers are being employed as a first nucleic acid part 12 and a second nucleic acid part 13 are shown in FIGS. 2A and 2B. FIG. 2A shows the state where a subject 11 to be analyzed does not bind to the nucleic acid element 16, and FIG. 2B shows the state where the subject 11 binds to the nucleic acid element 16. In FIGS. 2A and 2B, identical parts to those in FIGS. 1A and 1B are denoted by identical reference numerals.

As shown in FIGS. 2A and 2B, the nucleic acid element 16 is configured so that it includes: an aptamer as the first nucleic acid part 12; and an aptamer as the second nucleic acid part 13. The first nucleic acid part 12 is a subject-bindable nucleic acid molecule, and the second nucleic acid part 13 is a labeling substance-bindable nucleic acid molecule. The aptamer as the first nucleic acid part 12 and the aptamer as the second nucleic acid part 13 is formed into a single-stranded nucleic acid by linking to each other. A single-stranded RNA can be exemplified as the single-stranded nucleic acid, for example. One end of the first nucleic acid part 12 and one end of the second nucleic acid part 13 are directly linked to each other or indirectly linked to each other via a linker, for example. The linkage between the first nucleic acid part 12 and the second nucleic acid part 13 is not particularly limited. For example, the 5' end of the second nucleic acid part 13 may be linked to the 3' end of the first nucleic acid part 12, or the 3' end of the second nucleic acid part 13 may be linked to the 5' end of the first nucleic acid part 12.

As shown in FIG. 2A, when the subject 11 does not bind to the aptamer used as the first nucleic acid 12, a labeling substance 14 binds to the aptamer used as the second nucleic acid part 13. As shown in FIG. 1B, when the subject 11 binds to the aptamer used as the first nucleic acid part 12, the structure of the aptamer used as the second nucleic acid part 13 is changed, whereby the labeling substance 14 is separated from the aptamer used as the second nucleic acid part 13. In the case where the labeling substance 14 is an enzyme, the catalytic function of the enzyme is inhibited when the enzyme binds to the second nucleic acid part 13, for example. On the other hand, the inhibition of the catalytic function is removed when the enzyme as the labeling substance 14 is released from the second nucleic acid part 13. At that time, when a substrate is present, an enzyme reaction is generated by the catalytic function of the enzyme. Therefore, it becomes possible to analyze the subject 11 through analysis of the enzyme reaction.

FIGS. 2A and 2B are mere examples, and the present invention is by no means limited thereto. In the nucleic acid element 16, it is only necessary that, for example, the second nucleic acid part 13 can bind to the labeling substance 14 when the subject 11 does not bind to the first nucleic acid part 12, and the second nucleic acid part 13 cannot bind to the labeling substance 14 when the subject 11 binds to the first nucleic acid part 12, and there is no particular limitation for the rest.

Such a nucleic acid element for use in analysis using aptamers can be produced as follows, for example. First, an aptamer as a first nucleic acid part is obtained using a subject to be analyzed as a target. Further, an aptamer as a second nucleic acid part is obtained using, as a target, a labeling substance such as an enzyme, for example. As a method for obtaining the aptamers, the above-mentioned SELEX method can be employed. Then, these two aptamers are bound to each other. A method for binding the two aptamers to each other is not particularly limited, and can be, for example, a method in which sequences of the two aptamers are formed into a single-stranded nucleic acid sequence, and based on the single-stranded nucleic acid sequence, a nucleic acid is synthesized. In this case, for example, it may be possible that, by a computer or the like, the secondary structures of the two aptamers are predicted, and then the single-stranded nucleic acid sequence is revised, or a sequence is added or deleted.

Second Embodiment

A nucleic acid element for use in analysis of the second embodiment includes: a subject-bindable nucleic acid molecule as a first nucleic acid part; and a catalyst nucleic acid molecule as a second nucleic acid part. Specifically, the nucleic acid element includes: the first nucleic acid part; and the second nucleic acid part, the second nucleic acid part can generate a catalytic function of enzyme, the catalytic function of the second nucleic acid part is inhibited when the subject does not bind to the first nucleic acid part, and the inhibition of the catalytic function is removed when the subject binds to the first nucleic acid part.

The nucleic acid element is characterized in that the second nucleic acid part itself can generate the catalytic function of enzyme.

The nucleic acid element can be, for example, in a form in which the secondary structure of the second nucleic acid part is changed by binding the subject to the first nucleic acid part, and the second nucleic acid part generates the catalytic function by the change in the secondary structure of the second nucleic acid part. In the nucleic acid element, the catalytic function of the second nucleic acid part is inhibited when the subject does not bind to the first nucleic acid part, and the inhibition of the catalytic function is removed when the subject binds to the first nucleic acid part.

The first nucleic acid part may change its structure when the subject binds thereto, for example. Then, the structure of the second nucleic acid part is changed by the change in the structure of the first nucleic acid part, and the second nucleic acid part may generate the catalytic function by this change in the structure of the second nucleic acid part.

In the nucleic acid element, it is preferred that the catalytic function of the second nucleic acid part is controlled as follows, for example. That is, for example, in the nucleic acid element, the catalytic function is inactivated by caging the second nucleic acid part in the state where the subject does not bind to the first nucleic acid part. Then, the catalytic function is preferably activated by self-association of the second nucleic acid part when the subject binds to the first nucleic acid part.

The following form is shown as a specific example, for example. In the nucleic acid element, the following is preferable. For example, a part of the first nucleic acid part and a part of the second nucleic acid part form a stem structure in the state where the subject does not bind to the first nucleic acid part. Then, the second nucleic acid part is caged by the stem structure, so that the catalytic function is inactivated, and the first nucleic acid part forms a stem-loop structure as a binding site of binding the subject. On the other hand, the stem structure of the part of the first nucleic acid part and the part of the second nucleic acid part is removed by binding the subject to the first nucleic acid part, and thus, the casing of the second nucleic acid part is removed, and the catalytic function is activated by self-association of the second nucleic acid part.

When the nucleic acid element includes an intervening linker and an additional linker, it is preferred that the catalytic function of the second nucleic acid part is controlled as follows, for example. In the nucleic acid element, for example, one end of the intervening linker is linked to the 5' end of the first nucleic acid part, the other end of the intervening linker is linked to the 3' end of the second nucleic acid part, and the additional linker is, for example, linked to the 3' end of the first nucleic acid part. In the nucleic acid element, for example, the intervening linker and the 3' end region of the first nucleic acid part form a stem structure, and the additional linker and the 3' end region of the second nucleic acid part form a stem structure, in the state where the subject does not bind to the first nucleic acid part. Then, the second nucleic acid part is caged by the stem structures, so that the catalytic function is inactivated. Further, the first nucleic acid part forms a stem-loop structure as a binding site of binding the subject. On the other hand, the stem structure with the intervening linker and the stem structure with the additional linker are removed by binding the subject to the first nucleic acid part, and thus, the caging of the second nucleic acid part is removed, and the catalytic function is activated by self-association of the second nucleic acid part.

Examples of the nucleic acid element of the present embodiment are shown below. The present invention, however, is by no means limited thereto.

Figure 3A:
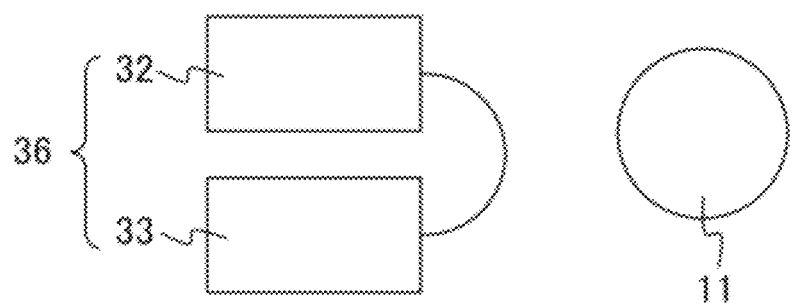
FIGS. 3A and 3B are explanatory drawings schematically illustrating a nucleic acid element for use in analysis of the second embodiment of the present invention.
Figure 3B:
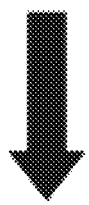
Figure 3B:
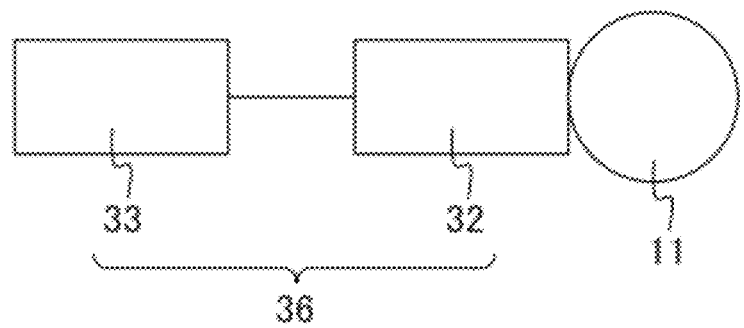

The configuration of the nucleic acid element is schematically shown in FIGS. 3A and 3B. FIG. 3A shows the state where the subject does not bind to the nucleic acid element, and FIG. 3B shows the state where the subject binds to the nucleic acid element.

As shown in FIGS. 3A and 3B, a nucleic acid element 36 for use in analysis is configured so that it includes: a first nucleic acid part (binding part) 32; and a second nucleic acid part (labeling part) 33. The first nucleic acid part 32 is a subject-bindable nucleic acid molecule, and the second nucleic acid part 33 is a catalyst nucleic acid molecule. The first nucleic acid part 32 and the second nucleic acid part 33 are integrated by linking to each other. One end of the first nucleic acid part 32 and one end of the second nucleic acid part 33 may be directly linked to each other or indirectly linked to each other via a linker, for example. The linkage between the first nucleic acid part 32 and the second nucleic acid part 33 is not particularly limited. For example, the 5' end of the second nucleic acid part 33 may be linked to the 3' end of the first nucleic acid part 32, or the 3' end of the second nucleic acid part 33 may be linked to the 5' end of the first nucleic acid part 32.

As shown in FIG. 3A, the second nucleic acid part 33 is associated with the first nucleic acid part 32 when the subject 11 does not bind to the first nucleic acid part 32, resulting in the state where the catalytic function is inhibited. As shown in FIG. 3B, the association between the first nucleic acid part 32 and the second nucleic acid part 33 is removed when the subject 11 binds to the first nucleic acid part 32, resulting in the state where the second nucleic acid part 33 can generate the catalytic function. At that time, when a substrate is present, a catalytic reaction is generated by the catalytic function of the second nucleic acid part 33. Therefore, it becomes possible to analyze the subject 11 through analysis of the catalytic reaction.

In the case where the second nucleic acid part 33 is a catalyst nucleic acid molecule that forms the structure of G-tetrad as mentioned above, the nucleic acid element is as follows, for example. When the subject 11 does not bind to the first nucleic acid part 32, the first nucleic acid part 32 and the second nucleic acid part 33 form a stem structure, so that the second nucleic acid part 33 is caged. Thus, the catalytic function of the second nucleic acid part 33 is inactivated. On the other hand, when the subject 11 binds to the first nucleic acid part 32, the secondary structure of the first nucleic acid part 32 is changed, and the stem structure of the first nucleic acid part 32 and the second nucleic acid part 33 is removed. Whereby, the second nucleic acid part 33 forms the G-tetrad by self-association and has a structure of G-quadruplex. For example, porphyrin is bound to the second nucleic acid part 33 having the structure of G-quadruplex, so that a composite of them is formed, and the catalytic function is activated.

The analysis of the catalytic reaction is not particularly limited and can be carried out in the same manner as in the first embodiment, for example. A method for analyzing the catalytic reaction is not particularly limited and may be, for example, optical detection or electrochemical detection. The optical detection can be, for example, detection of an optical signal such as a developed color or emitted light and can be carried out by measuring a signal intensity such as an absorbance, a reflectance, or a fluorescence intensity. The optical signal is generated by carrying out the catalytic reaction in the presence of a substrate, for example. The substrate is not particularly limited and is preferably a substrate that develops a color or emits light by the catalytic reaction. The electrochemical detection can be, for example, detection of an electrochemical signal and can be carried out by measuring a signal intensity such as a current. The electrochemical signal is generated, as the transfer of electrons, by carrying out the catalytic reaction in the presence of a substrate, for example. The transfer of electrons can be measured as a current through applying a voltage to electrodes, for example. In the case of the detection of an electrochemical signal, for example, the enzyme reaction may be carried out in the presence of the substrate and a mediator, and at that time, the transfer of electrons between the enzyme and the mediator may be measured.

The type of the catalytic function of the second nucleic acid part 33 is not particularly limited and can be, for example, the same as the catalytic function of the enzyme in the nucleic acid element of the first embodiment. A nucleic acid molecule that can generate the catalytic function can be, for example, DNA having Heminperoxidase activity (Tao et al, Anal. Chem., 2009, 81, 2144-2149). Moreover, the substrate is not particularly limited and can be, for example, the substrate used in the first embodiment.

Figure 4A:
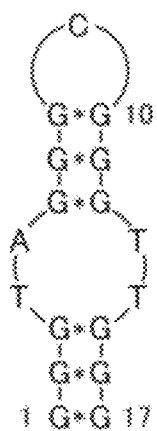
FIGS. 4A to 4D show a specific example of an analytical method using the nucleic acid element of the second embodiment.
Figure 4B:
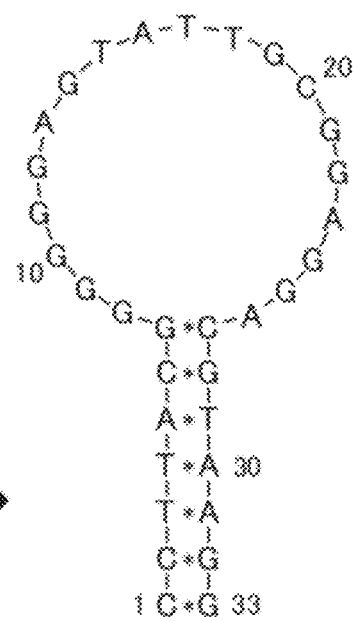
Figure 4C:
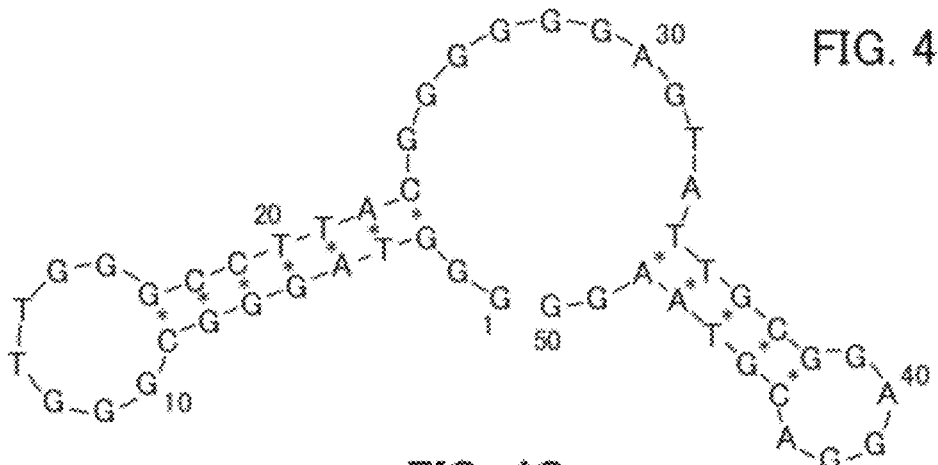
Figure 4D:
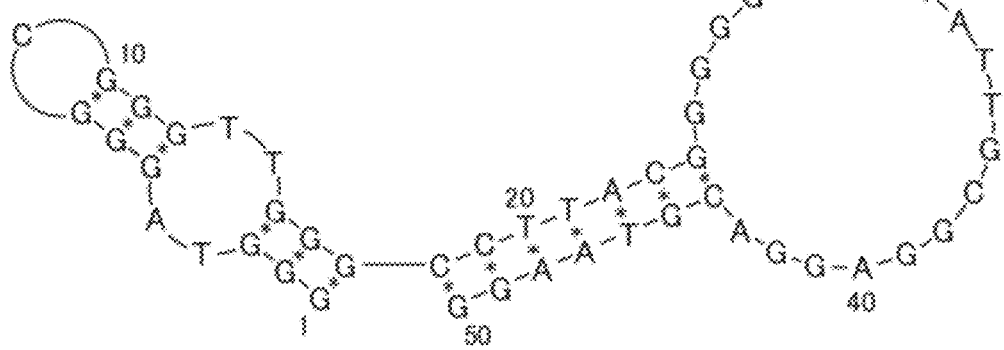

Next, an example of a nucleic acid element for use in analysis, including: an aptamer employed as a first nucleic acid part 32; and DNA that can generate peroxidase activity, employed as a second nucleic acid part 33, is shown below. In FIGS. 4A to 4D, FIG. 4A is DNA (SEQ ID NO: 1) that can generate peroxidase activity, and FIG. 4B is an aptamer (SEQ ID NO: 2) against adenosine. FIG. 4C is a single-stranded nucleic acid element (SEQ ID NO: 3) obtained by binding the DNA (A) to the aptamer (B) for use in analysis. In the nucleic acid element shown in FIG. 4C, the aptamer (B) does not bind to adenosine, so that the DNA (A) has a secondary structure by which a catalytic function is not generated. Then, by binding adenosine to the aptamer (B) in the nucleic acid element, the secondary structure of the DNA shown in FIG. 4C is changed to a secondary structure (SEQ ID NO: 3) with which the catalytic function can be generated as shown in FIG. 4D. At that time, when a substrate is present, a catalytic reaction is generated by the catalytic function of the DNA. Therefore, it becomes possible to analyze the adenosine as a subject to be analyzed through analysis of the catalytic reaction by the DNA.

This nucleic acid element can be used in measurements of viable cells in food, for example. The presence of viable cells in food means the presence of ATP. Therefore, the concentration of ATP is proportional to the viable cell count. Thus, by causing a chromogenic substrate to react with food using this nucleic acid element, a color proportional to the concentration of ATP derived from viable cells is developed. The viable cell count in food can be analyzed through analysis of this developed color. This is a mere example and the use of the nucleic acid element of the present invention is by no means limited thereto.

This nucleic acid element can be produced as follows, for example. First, an aptamer as a first nucleic acid part is obtained using a subject to be analyzed as a target. As a method for obtaining the aptamer, the above-mentioned SELEX method can be employed. Further, the sequence of a second nucleic acid part is designed and synthesized according to a desired catalytic function, for example. Then, the aptamer of the first nucleic acid part and the second nucleic acid part are bound to each other. A method for binding the aptamer of the first nucleic acid part and the second nucleic acid part to each other is not particularly limited and can be, for example, a method in which the sequence of the aptamer of the first nucleic acid part and the sequence of the second nucleic acid part are formed into a single-stranded nucleic acid sequence, and based on the single-stranded nucleic acid sequence, a nucleic acid is synthesized. In this case, for example, it may be possible that, by a computer or the like, the secondary structures of the first nucleic acid part, the second nucleic acid part and/or the single-stranded nucleic acid are predicted, and then the sequence of the single-stranded nucleic acid sequence is revised, or a sequence is added or deleted.

<Analytical Reagent>

The analytical reagent of the present invention contains the nucleic acid element of the present invention.

Examples of the nucleic acid element in the analytical reagent of the present invention include the nucleic acid elements of the first embodiment and the second embodiment.

When the analytical reagent of the present invention contains the nucleic acid element of the first embodiment, it is preferred that the analytical reagent further contains a labeling substance. The labeling substance is not particularly limited and is the same as mentioned above, and among them, an enzyme is preferable. When the labeling substance is an enzyme, it is preferred that the analytical reagent of the present invention may further contain a substrate for the enzyme. The substrate is not particularly limited and may be the same as mentioned above, and among them, a chromogenic substrate that develops a color by a reaction of the enzyme is preferable. The chromogenic substrate is the same as mentioned above.

When the analytical reagent of the present invention contains the nucleic acid element of the second embodiment, it is preferred that the analytical reagent further contains a substrate. The substrate is not particularly limited and is the same as mentioned above. The substrate is preferably a chromogenic substrate that develops a color by a reaction caused by a catalytic function of the catalyst nucleic acid molecule used as the second nucleic acid part of the nucleic acid element. The chromogenic substrate is the same as mentioned above.

The analytical reagent of the present invention may be, for example, an analytical kit. In this case, the analytical reagent may contain the nucleic acid element of the present invention and other component, and they may be stored in individual containers or may be stored in the same container. Examples of the other component include the labeling substance, the substrate, porphyrin, a buffer solution, and various additives. The other component may be added to the nucleic acid element when the nucleic acid element is used, for example. The analytical kit may further include instructions thereof, for example.

<Analytical Instrument>

The analytical instrument of the present invention includes the analytical reagent of the present invention. It is only necessary that the analytical instrument of the present invention includes the nucleic acid element of the present invention as the analytical reagent of the present invention, and the other configuration is not particularly limited. The analytical instrument of the present invention is the same as the nucleic acid element and the analytical reagent unless otherwise shown.

In the analytical instrument of the present invention, the nucleic acid element may be, for example, the nucleic acid element of the first embodiment or the second embodiment. In the case of the nucleic acid element of the first embodiment, the nucleic acid element in which the labeling substance is bound to the second nucleic acid part, i.e., the labeling substance-bindable nucleic acid molecule in advance is preferred.

The analytical instrument of the present invention may include only one type of the nucleic acid element or two or more types of the nucleic acid elements each having a different target, for example. In the latter case, for example, it is preferred that each of the two or more types of the nucleic acid elements has a first nucleic acid part that can bind to a different target. As described above, when the analytical instrument of the present invention includes two types of the nucleic acid elements each having a different target, it becomes possible to detect two or more types of subjects to be analyzed in one analytical instrument, for example. When the analytical instrument of the present invention includes two or more types of the nucleic acid elements, it is preferred that the analytical instrument includes a plurality of detection parts, and the nucleic acid elements are arranged in the respective detection parts.

The shape of the analytical instrument of the present invention is not particularly limited, and examples thereof include a bag-shaped container, a stick-shaped container, a tube-shaped container, and a chip-shaped container.

The analytical reagent is arranged on the inner surface of the container of the analytical instrument of the present invention, for example. Specifically, the nucleic acid element of the present invention is arranged on the same. In the analytical instrument of the present invention, other component may further be arranged, for example. Examples of the other component include the substrate, the porphyrin, a buffer agent, and a solvent. Examples of the solvent include water, a buffer solution, and a saline solution. The other component may be added to the container when the analytical instrument is used, for example.

The analytical instrument of the present invention may further include a positive control in order to improve reliability of analysis, for example. It is preferred that the positive control is arranged on the inner surface of the container, for example.

Specific examples of the analytical instrument are described below. The present invention, however, is by no means limited thereto.

Third Embodiment

Figure 5A:
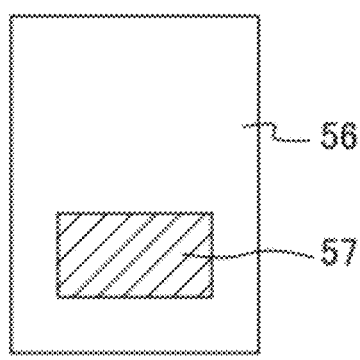
FIGS. 5A to 5C are explanatory drawings schematically illustrating an analytical method using an analytical instrument of the third embodiment of the present invention.
Figure 5B:
Figure 5B:
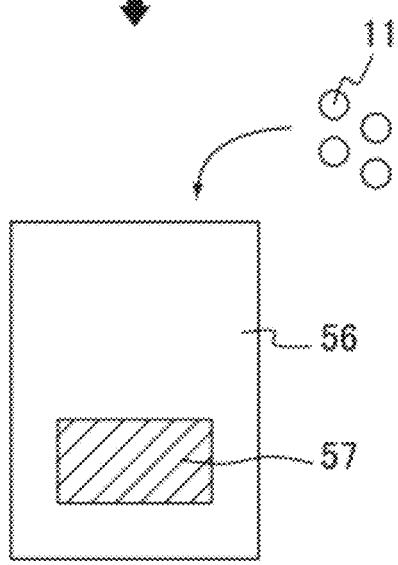
Figure 5C:
Figure 5C:
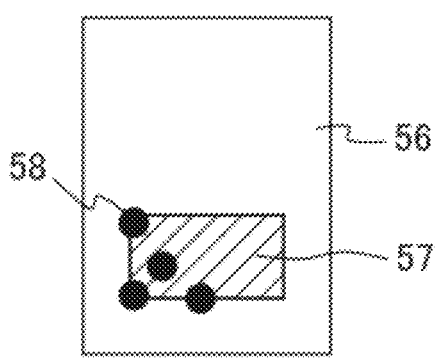

An analytical instrument of the third embodiment is an example of a bag-shaped analytical instrument. FIGS. 5A to 5C show a bag-shaped analytical instrument 56 of the present embodiment. As shown in FIG. 5A, a reagent layer 57 including a nucleic acid element for use in analysis is arranged on the inner surface of the bag-shaped analytical instrument 56. When the nucleic acid element of the first embodiment is used, the reagent layer 57 preferably includes the nucleic acid element, an enzyme as a labeling substance, and a substrate (e.g., a chromogenic substance). When the nucleic acid element of the second embodiment is used, the reagent layer 57 preferably includes the nucleic acid element and a substrate (e.g., a chromogenic substance) and more preferably may further include porphyrin. The reagent layer 57 may further include, besides them, a buffer agent, a hydrophilic polymer, or the like. The reagent layer 57 can be formed as follows, for example. A reagent solution containing the nucleic acid element, an enzyme, a substrate, and other component is prepared, and the reagent solution is applied to the inner surface of a bag-shaped container, which was then dried.

When a subject 11 to be analyzed is placed in the bag-shaped analytical instrument 56 as shown in FIG. 5B, the subject 11 reacts with the nucleic acid element in the reagent layer 57, and the substrate develops a color 58 as shown in FIG. 5C. The subject 11 can be analyzed through analysis of this developed color 58. The developed color can be analyzed by visual check or may be analyzed using an optical detection device, for example. In the latter case, for example, an optical signal such as an absorbance, a reflectance, or the like may be measured.

As mentioned above, the analytical instrument of the present invention is not limited to a bag-shaped analytical instrument and may be a stick-shaped analytical instrument, for example. In the case of the stick-shaped analytical instrument, the reagent layer may be formed by using a porous member such as a filter paper and immersing the porous member in the reagent solution and drying the resultant porous member as mentioned above, for example.

Fourth Embodiment

An analytical instrument of the fourth embodiment is an example of an analytical instrument used in electrochemical detection, specifically an example of an analytical instrument including the nucleic acid element of the second embodiment, which can generate the catalytic function of an oxidation-reduction reaction. The analytical instrument of the present embodiment includes: a basal plate, the nucleic acid element, and a detection part of detecting an electrical signal, the nucleic acid element and the detection part are arranged on the basal plate, and the detection part is a detection part of detecting an electrical signal generated by the oxidation-reduction reaction caused by the second nucleic acid part.

The basal plate is not particularly limited and is, for example, preferably a basal plate having insulation properties on the surface thereof, for example. The basal plate may be a basal plate composed of an insulating material or a basal plate having, on the surface thereof, an insulating layer composed of an insulating material. The insulating material is not particularly limited, and examples thereof include conventionally known materials such as glass, ceramics, an insulating plastic, and paper. The insulating plastic is not particularly limited, and examples thereof include a silicone resin, a polyimide resin, an epoxy resin, and a fluorine resin.

It is only necessary that the detection part can detect an electrical signal generated by an oxidation-reduction reaction caused by the second nucleic acid part. The detection part has an electrode system, for example. The electrode system may include a working electrode and a counter electrode, or may include a working electrode, a counter electrode, and a reference electrode, for example. The materials of the electrodes are not particularly limited, and examples thereof include platinum, silver, gold, and carbon. Examples of the working electrode and the counter electrode include a platinum electrode, a silver electrode, a gold electrode, and a carbon electrode. The reference electrode can be, for example, a silver/silver chloride electrode. The silver/silver chloride electrode can be formed by laminating a silver chloride electrode on a silver electrode, for example.

The detection part can be formed by arranging the electrodes on the upper surface of the basal plate, for example. A method for arranging the electrodes is not particularly limited, and for example, a conventionally known method can be employed. Specific examples of the method include thin-film forming methods such as an evaporation method, a sputtering method, a screen printing method, and a plating method. The electrodes may be arranged directly or indirectly on the basal plate, for example. The indirect arrangement can be, for example, arrangement via other member (the same applies hereinafter).

As mentioned above, it is only necessary that the nucleic acid element is arranged on the basal plate. It is, however, preferred that the nucleic acid element is immobilized on the basal plate. The nucleic acid element may be arranged directly or indirectly on the surface of the basal plate, for example. Specifically, for example, the nucleic acid element is arranged preferably on the detection part of the basal plate, more preferably on the electrodes in the detection part, and yet more preferably on the working electrode among the electrodes. The nucleic acid element may be arranged directly or indirectly on the detection part or the electrodes, for example. Hereinafter, the "arrangement or immobilization of the nucleic acid element on the basal plate" encompasses the arrangement or immobilization of the nucleic acid element on the detection part in the basal plate or on the electrodes in the detection part unless otherwise shown.

A method for arranging the nucleic acid element is not particularly limited, and a conventionally known method for immobilizing a nucleic acid can be employed. The method for immobilizing a nucleic acid can be, for example, a method for immobilizing a pre-prepared nucleic acid on the basal plate, preferably on the detection part, more preferably on the electrodes. This method is, for example, a method utilizing photolithography, and a specific example thereof can be found in references such as U.S. Pat. No. 5,424,186 and the like. Furthermore, a method for immobilizing a nucleic acid can be, for example, a method for synthesizing a nucleic acid on the basal plate, preferably on the detection part, more preferably on the electrodes. This method can be, for example, a spot method, and a specific example thereof can be found in references such as U.S. Pat. No. 5,807,522 and JP H10-503841 A.

In the nucleic acid element, the basal plate may be arranged on one end side of the first nucleic acid part or the second nucleic acid part, for example. The one end side is, for example, one end of the first nucleic acid part or second nucleic acid part in the nucleic acid element. When the first nucleic acid part has an additional linker, the one end side may be, for example, the end of the additional linker, opposite to the end to which the first nucleic acid part is linked. On the other hand, when the second nucleic acid part has an additional linker, the one end side may be, for example, the end of the additional linker, opposite to the end to which the second nucleic acid part is linked, and this form is preferable.

The analytical instrument may include a plurality of the nucleic acid elements, for example. Such an analytical instrument can be formed by, for example, fractionating the surface of the basal plate into matrixes, forming the above-mentioned electrode systems in the respective fraction regions, and arranging nucleic acid elements in the respective resultant fraction regions as detection parts.

A specific example of the analytical instrument of the present embodiment is shown below. The present invention, however, is by no means limited thereto.

Figure 6:
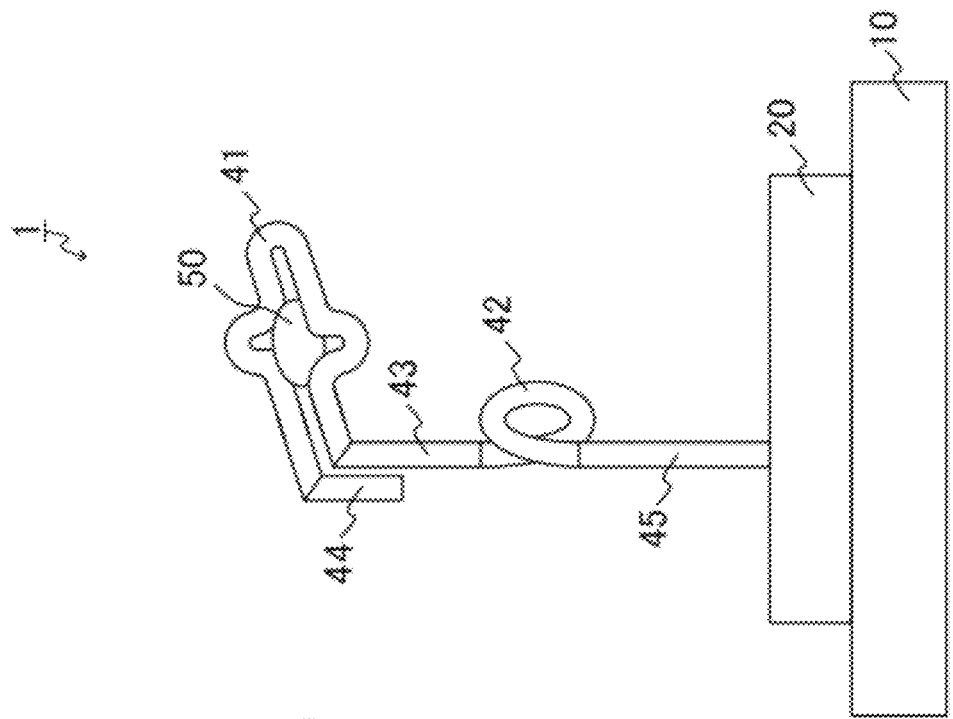
FIG. 6 shows a specific example of an analytical method using an analytical instrument of the fourth embodiment of the present invention.
Figure 6:
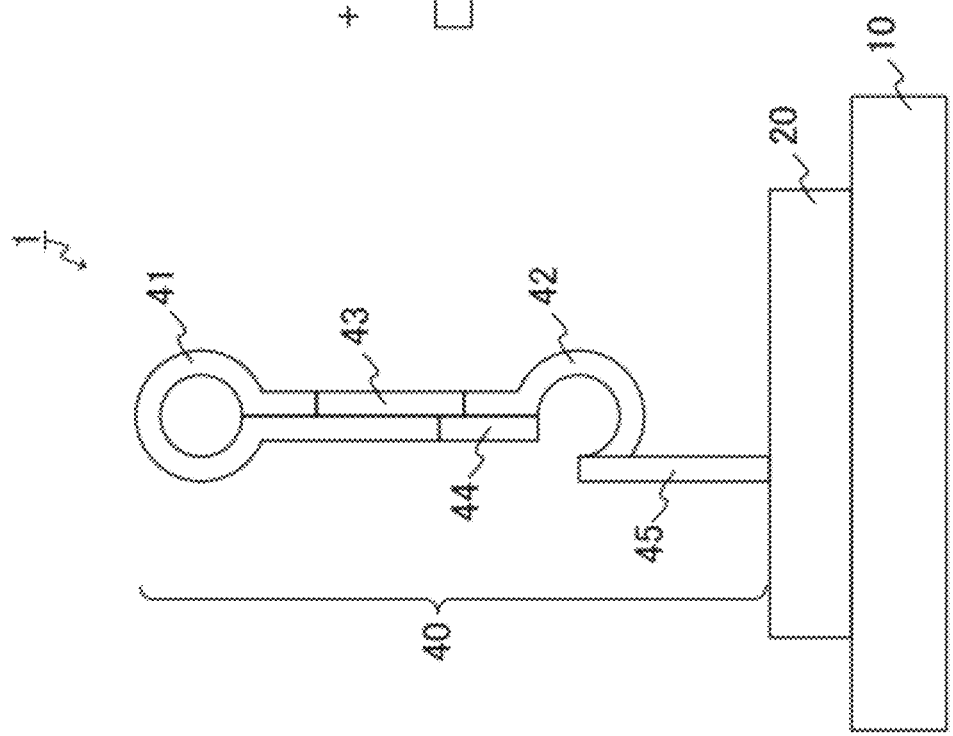

The configuration of the analytical instrument is schematically shown in FIG. 6. In FIG. 6, the drawing on the left side shows the state where the nucleic acid element in the analytical instrument does not bind to the subject, and the drawing on the right side shows the state where the nucleic acid element in the analytical instrument binds to the subject.

As shown in FIG. 6, an analytical instrument 1 includes a basal plate 10, an electrode 20, and a nucleic acid element 40 for use in analysis, the electrode 20 is arranged on the basal plate 10, and the nucleic acid element 40 is immobilized on the electrode 20. A region of the basal plate 10, on which the electrode 20 is arranged, is a detection part. The nucleic acid element 40 is a single-stranded nucleic acid composed of a first nucleic acid part 41, a second nucleic acid part 42, an intervening linker 43, a first additional linker 44, and a second additional linker 45. In the nucleic acid element 40, the first nucleic acid part 41 and the second nucleic acid part 42 are linked to each other via the intervening linker 43, the first additional linker 44 is linked to one end of the first nucleic acid part 41, and the second additional linker 45 is linked to one end of the second nucleic acid part 42. Further, the nucleic acid element 40 is immobilized on the electrode 20 via the second additional linker 45 linking to the second nucleic acid part 42. It is preferred that the first nucleic acid part 41 is a single strand and forms a stem-loop structure by self-annealing as shown in the drawing on the left side of FIG. 6 in the state where the first nucleic acid part does not bind to the subject.

A method for using the analytical instrument 1 is described with taking a case in which an aptamer that can bind to the subject 50 is used as the first nucleic acid part 41, and DNA that can generate peroxidase activity is used as the second nucleic acid part 42 as an example.

First, a sample and a reagent are added to a detection part of the analytical instrument 1. The reagent contains a substrate and porphyrin. As shown in the drawing on the left side of FIG. 6, the subject 50 does not bind to the first nucleic acid part 41 of the nucleic acid element 40 when the sample contains no subject 50, so that the second nucleic acid part 42 does not generate peroxidase activity. Specifically, when the second nucleic acid part 42 forms a stem structure with the first additional linker 44, the second nucleic acid part 42 is caged, and the catalytic function of the second nucleic acid part 42 is inactivated. Therefore, no transfer of electrons is generated by the second nucleic acid part 42. Thus, an electrical signal cannot be detected with the electrode 20 in the detection part. In contrast, the subject 50 binds to the first nucleic acid part 41 of the nucleic acid element 40 as shown in the drawing on the right side of FIG. 6 when the subject 50 is present in the sample, so that the structure of the second nucleic acid part 42 is changed to the secondary structure with which peroxidase activity is generated. Specifically, when the subject 50 binds to the first nucleic acid part 41, the structure of the first nucleic acid part 41 is changed, and the stem structure of the second nucleic acid part 42 and a first additional linker 44 is removed. Whereby, the second nucleic acid part 42 forms the G-tetrad by self-association and has a structure of G-quadruplex. Porphyrin is bound to the second nucleic acid part 42 having the structure of G-quadruplex, so that a composite of them is formed, and the catalytic function is activated. Then, the transfer of electrons is generated by the activated second nucleic acid part 42 in the step of generating a product from the substrate. Thus, an electrical signal can be detected with the electrode 20 in the detection part. As described above, according to the analytical instrument 1, the presence or absence of the subject in the sample can be analyzed through detection of an electrical signal.

The reagent may further contain the mediator, for example. With respect to the reagent, a reagent solution containing the various reagents may be added to the analytical instrument before, at the same time of, or after adding a sample to the analytical instrument.

<Analytical Method>

The analytical method of the present invention is characterized in that the nucleic acid element of the present invention is used, a subject to be analyzed is bound to a first nucleic acid part, and the binding is analyzed by a second nucleic acid part. The analytical method of the present invention can be carried out by the method mentioned for the nucleic acid element, analytical instrument, and the like of the present invention, unless otherwise shown.

The nucleic acid element used in the analytical method of the present invention is the same as mentioned above, and examples thereof include the nucleic acid elements of the first embodiment and the second embodiment.

When the nucleic acid element of the first embodiment is used in the analytical method of the present invention, the binding is analyzed as follows, for example. That is, for example, it is preferred that, before analysis, a labeling substance is bound to the second nucleic acid part, and in analysis, the labeling substance is released from the second nucleic acid part by binding the subject to the first nucleic acid part, and the released labeling substance is analyzed. In this case, for example, the secondary structure of the second nucleic acid part is changed by binding the subject to the first nucleic acid part, and the labeling substance binding to the second nucleic acid part is released from the second nucleic acid part by the change in the secondary structure.

The labeling substance is not particularly limited and can be the same as mentioned above, and among them, an enzyme is preferable. In the case where the labeling substance is an enzyme, the catalytic function of the enzyme is inhibited when the enzyme binds to the second nucleic acid part, and the inhibition of the catalytic function of the enzyme is removed when the enzyme is released from the second nucleic acid part, for example. Then, an enzyme reaction caused by the catalytic function of the enzyme is analyzed in the analysis. The enzyme binding to the second nucleic acid part is released from the second nucleic acid part by binding the subject to the first nucleic acid part, for example.

In this case, a method for analyzing the binding is not particularly limited and can be carried out by analysis of the released labeling substance, for example. The analysis of the released labeling substance can be set as appropriate according to the type of the labeling substance. When the labeling substance is the enzyme, the analysis can be carried out through analysis of an enzyme reaction of the released enzyme, for example. A method for analyzing the enzyme reaction is not particularly limited and may be optical detection or electrochemical detection, for example. The optical detection can be, for example, detection of an optical signal such as a developed color or emitted light and can be carried out by measuring a signal intensity such as an absorbance, a reflectance, or a fluorescent intensity. The optical signal is generated by the enzyme reaction in the presence of the substrate, for example. The substrate is not particularly limited and is, for example, preferably a substrate that develops a color or emits light by the enzyme reaction. The electrochemical detection can be, for example, detection of an electrochemical signal and can be carried out by measuring a signal intensity such as a current. The electrochemical signal is generated, as transfer of electrons, by the enzyme reaction in the presence of a substrate, for example. The transfer of electrons can be measured as a current through applying a voltage to electrodes, for example.

The timing of adding the substrate is not particularly limited, and for example, the substrate and the nucleic acid element may be present together in advance, or the substrate may be added together with a sample to be analyzed when the subject is bound to the first nucleic acid part or may be added after adding the sample to be analyzed, for example.

When the nucleic acid element of the second embodiment is used in the analytical method of the present invention, the binding is analyzed as follows, for example. That is, for example, it is preferred that in analysis, the catalytic function of the second nucleic acid part is generated by binding the subject to the first nucleic acid part, and a reaction caused by the catalytic function is analyzed. In this case, for example, the secondary structure of the second nucleic acid part is changed by binding the subject to the first nucleic acid part, and the catalytic function of the second nucleic acid part is generated by the change in the secondary structure.

In this case, a method for analyzing the binding is not particularly limited and can be carried out by analysis of a catalytic reaction caused by the catalytic function of the second nucleic acid part, for example. The analysis of the catalytic reaction can be set as appropriate according to the type of the catalytic function of the second nucleic acid part. A method for analyzing a reaction caused by the catalytic function is not particularly limited and may be, for example, optical detection or electrochemical detection. The optical detection can be, for example, detection of an optical signal such as a developed color or emitted light and can be carried out by measuring a signal intensity such as an absorbance, a reflectance, or a fluorescent intensity. The optical signal is generated by the catalytic reaction in the presence of the substrate, for example. The substrate is not particularly limited and is, for example, preferably a substrate that develops a color or emits light by the catalytic reaction. The electrochemical detection can be, for example, detection of an electrochemical signal and can be carried out by measuring a signal intensity such as a current. The electrochemical signal is generated, as transfer of electrons, by the catalytic reaction in the presence of a substrate, for example. The transfer of electrons can be measured as a current through applying a voltage to electrodes, for example.

The timing of adding the substrate is not particularly limited, and for example, the substrate and the nucleic acid element may be present together in advance, or the substrate may be added at the time of or after adding a sample to be analyzed, for example.

When the nucleic acid element of the second embodiment is used, it is preferred that the catalytic reaction is carried out in the presence of porphyrin, for example. The timing of adding the porphyrin is not particularly limited, and for example, the porphyrin and the nucleic acid element may be present together in advance, or the porphyrin may be added together with a sample to be analyzed or after adding the sample to be analyzed, for example.

The analytical method of the present invention can be carried out by using also the above-mentioned analytical reagent and analytical instrument of the present invention and the like, for example.

The invention of the present application is described above with reference to the Embodiments and Examples. However, various changes that can be understood by those skilled in the art can be made in the configurations and details of the invention within the scope of the invention of the present application.

This application claims priority from Japanese Patent Application No. 2009-185283 filed on Aug. 7, 2009. The entire subject matter of the Japanese Patent Applications is incorporated herein by reference.

INDUSTRIAL APPLICABILITY

The present invention can develop a simple detection system. The use thereof is not limited and can be applied to a wide range of field such as a food field, a medical field, an agriculture field, and an environment field, for example.

EXPLANATION OF REFERENCE NUMERALS 1 analytical instrument
10 basal plate
11, 50 subject to be analyzed
12, 32, 41 first nucleic acid part
13, 33, 42 second nucleic acid part
14 labeling substance
16, 36, 40 nucleic acid element for use in analysis
20 electrode
43 intervening linker
44 first additional linker
45 second additional linker
56 bag-shaped analytical instrument
57 reagent layer
58 color development

The invention claimed is:

1. A nucleic acid element for use in analysis, the nucleic acid element comprising:
   a first nucleic acid part; and
   a second nucleic acid part, wherein
   the first nucleic acid part is an aptamer that can bind to a subject to be analyzed, wherein the subject to be analyzed is not an enzyme,
   the second nucleic acid part is a DNAzyme or an RNAzyme that can be detected to distinguish between binding and non-binding of the first nucleic acid part to the subject,
   a catalytic function of the DNAzyme or the RNAzyme of the second nucleic acid part is inhibited when the subject does not bind to the first nucleic acid part,
   the inhibition of the catalytic function is removed when the subject binds to the first nucleic acid part,
   the first nucleic acid part and the second nucleic acid part are linked to each other to form a single-stranded nucleic acid,
   a part of the first nucleic acid part and a part of the second nucleic acid part associate with each other to form a stem structure in a state where the subject does not bind to the first nucleic acid part, such that the second nucleic acid part is caged by the stem structure and the catalytic function of the DNAzyme or the RNAzyme of the second nucleic acid part is inactivated;
   the structure of the second nucleic acid part is changed by the change in the structure of the first nucleic acid part, and the second nucleic acid part generates the catalytic function by this change in the structure of the second nucleic acid part; and
   both the first nucleic acid part and the second nucleic acid part have a secondary structure.

2. The nucleic acid element of claim 1, wherein the second nucleic acid part is a nucleic acid that can generate a catalytic function of peroxidase.

3. An analytical reagent comprising the nucleic acid element of claim 1.

4. The analytical reagent of claim 3, comprising:
   in the nucleic acid element the second nucleic acid part can generate a catalytic function of enzyme,
   the catalytic function of the second nucleic acid part is inhibited when the subject does not bind to the first nucleic acid part, and
   the inhibition of the catalytic function is removed when the subject binds to the first nucleic acid part; and
   a substrate,
   wherein the substrate is used in a reaction caused by a catalytic function of the second nucleic acid part.

5. The analytical reagent of claim 4, wherein the substrate is a chromogenic substrate that develops a color by a reaction caused by the catalytic function.

6. The analytical reagent of claim 4, further comprising porphyrin.

7. An analytical instrument comprising the analytical reagent of claim 3.

8. The analytical instrument of claim 7, wherein the analytical reagent is arranged on the inner surface of the analytical instrument.

9. The analytical instrument of claim 7, further comprising a positive control.

* * * * *

SEQUENCE LISTING

```
<160> NUMBER OF SEQ ID NOS: 3

<210> SEQ ID NO 1
<211> LENGTH: 17
<212> TYPE: DNA
<213> ORGANISM: Artificial Sequence
<220> FEATURE:
<223> OTHER INFORMATION: Synthetic DNA

<400> SEQUENCE: 1
gggtagggcg ggttggg                                                    17

<210> SEQ ID NO 2
<211> LENGTH: 33
<212> TYPE: DNA
<213> ORGANISM: Artificial Sequence
<220> FEATURE:
<223> OTHER INFORMATION: Synthetic DNA

<400> SEQUENCE: 2
ccttacgggg ggagtattgc ggaggacgta agg                                  33

<210> SEQ ID NO 3
<211> LENGTH: 50
<212> TYPE: DNA
<213> ORGANISM: Artificial Sequence
```

```
<220> FEATURE:
<223> OTHER INFORMATION: Synthetic DNA

<400> SEQUENCE: 3
gggtagggcg ggttgggcct tacgggggga gtattgcgga ggacgtaagg            50
```